(12) United States Patent
Schmidt

(10) Patent No.: US 6,748,951 B1
(45) Date of Patent: Jun. 15, 2004

(54) ANTI-SNORING DEVICES AND METHODS

(76) Inventor: Bruno Schmidt, 5836 Portsmouth Dr., Tampa, FL (US) 33315

( * ) Notice: Subject to any disclaimer, the term of this patent is extended or adjusted under 35 U.S.C. 154(b) by 0 days.

(21) Appl. No.: 10/460,349

(22) Filed: Jun. 13, 2003

Related U.S. Application Data

(60) Division of application No. 10/266,160, filed on Oct. 8, 2002, which is a continuation-in-part of application No. 09/967,540, filed on Oct. 1, 2001, now Pat. No. 6,467,485.

(51) Int. Cl.[7] ................................................. A61F 5/56
(52) U.S. Cl. .................. 128/848; 602/902; 606/204.25
(58) Field of Search ............................. 128/846, 848, 128/859–862; 602/902; 606/199, 204.25; 433/6

(56) References Cited

U.S. PATENT DOCUMENTS

| | | | | |
|---|---|---|---|---|
| 5,666,973 A | * | 9/1997 | Walter | 128/861 |
| 5,915,385 A | * | 6/1999 | Hakimi | 128/859 |
| 5,988,170 A | * | 11/1999 | Thomas | 128/848 |
| 6,250,307 B1 | * | 6/2001 | Conrad | 128/898 |
| 6,546,936 B2 | * | 4/2003 | Knudson | 128/898 |

* cited by examiner

Primary Examiner—Michael A. Brown
(74) Attorney, Agent, or Firm—Stanley M Miller

(57) ABSTRACT

A first method for inhibiting snoring includes at least one layer of adhesive that is applied to a soft pallet to prevent vibration of the soft pallet. A second method employs a transdermal patch having an astringent or muscle-contracting drug thereon that is applied to the soft pallet. In a third method, the astringent or muscle-contracting drug is snorted by the user. In a fourth method, the astringent or muscle-contracting drug is applied to the soft pallet by an atomized nasal spray. In a fifth embodiment, a thin electrical device is positioned against the hard pallet in electrical communication with a pair of closely spaced apart electrodes that abut the soft pallet. A low, safe current between the electrodes stiffens the soft pallet and prevents it from fluttering. A denture-like device may be used to hold the thin electrical device in place.

5 Claims, 3 Drawing Sheets

ANTI-SNORING DEVICES AND METHODS

CROSS REFERENCE TO RELATED APPLICATIONS

This application is a Div of Ser. No. 10/266,160 Oct. 8, 2002 which is a continuation-in-part application of application Ser. No. 09/967,540, filed Oct. 1, 2001 now U.S. Pat. No. 6,467,485, entitled "Anti-Snoring Device and Method", by the present inventor.

BACKGROUND OF THE INVENTION

1. Field of the Invention

This invention relates, generally, to devices and methods that help people stop snoring during sleep. More specifically, it relates to devices and methods that inhibit vibration of the soft pallet as air flows past it.

2. Description of the Prior Art

It is known that certain surgical techniques can eliminate the cause of snoring in some people. However, surgery is a rather drastic, expensive remedy that is not without risk.

A well-known anti-snoring treatment available over-the-counter is an oil solution that is sprayed onto the back of the mouth. The oil mixture includes olive oil, sunflower oil, almond oil, peppermint oil, and the like. Oil soluble vitamins such as Vitamin E may also be provided in the solution. The oil apparently lubricates the soft pallet at the back of the mouth and perhaps the tongue as well and such lubrication solves the problem for some people. However, some people report unsatisfactory results with such oils.

Some people snore because they are overweight. In an effort to lose weight, they lower their intake of high fat foods. Accordingly, the addition of approximately one teaspoon a day of high fat oil is undesirable.

Mechanical devices that suppress the tongue are also commercially available. These devices are about the size of a mouthpiece of the type worn by athletes engaged in contact sports. Many people find it difficult to sleep at night with such a device in their mouth. However, most of those who persist until they get used to the device are satisfied with the results.

What is needed, then, are non-surgical alternatives to oil-based and mouthpiece-reliant remedies. The alternative remedies should not require the user to ingest high fat oils or to get used to sleeping with a bulky mechanical structure in the mouth. Moreover, the alternative treatments should be effective, inexpensive and easy to use.

However, in view of the prior art taken as a whole at the time the present invention was made, it was not obvious to those of ordinary skill in this art how the needed devices and methods could be provided.

SUMMARY OF THE INVENTION

The long-standing but heretofore unfulfilled need for non-surgical alternative snoring-suppressing devices and methods that do not rely upon oils and mouthpieces is now met by a new, useful, and nonobvious invention that is provided in five embodiments. Some of the five embodiments may be used with one another, i.e., the embodiments are not necessarily mutually exclusive although some of them are best used alone and not in conjunction with other devices and methods.

In a first embodiment, the soft pallet is made more rigid by the application thereto of a suitable adhesive. The increased rigidity inhibits fluttering of the soft pallet as the user breathes.

In a second embodiment, the soft pallet is made more rigid by application of an astringent or muscle-contracting drug delivered by a transdermal patch.

In a third embodiment, the astringent or muscle-contracting drug is provided in a powder form and "snorted" by the user so that it overlies the soft pallet.

In a fourth embodiment, the astringent or muscle-contracting drug is applied to the soft pallet by an atomized nasal spray.

In a fifth embodiment, a thin electrical device includes two conductors that extend or project outwardly from the transdermal patch. The electrical device is glued onto the hard pallet in such a way that the conductors extend into contacting relation with and rest against the soft pallet. The electrical device includes a low power DC source that generates a safe muscle-contracting current between the conductors to contract the soft pallet and thereby inhibit snoring.

A soft plastic device fits over the upper teeth and a web part thereof covers the roof of the mouth and retains the electrical device in sandwiched relation between the hard pallet and the web part. Moreover, the electrical device may be permanently affixed to the top of the webbing and the soft plastic device may be affixed to the hard pallet and teeth with a commercially available denture adhesive.

The primary object of this invention is to significantly advance the art of anti-snoring devices and methods.

A more specific object is to provide a method where snoring is inhibited by various means that are applied to the soft pallet and which prevent said soft pallet from vibrating when air passes thereover.

Another important object is to provide a method that harnesses the ability of very low electrical currents to contract the soft pallet so that it does not vibrate when air passes over it.

The invention accordingly comprises the features of construction, combination of elements, and arrangement of parts that will be exemplified in the description set forth hereinafter, and the scope of the invention will be set forth in the claims.

BRIEF DESCRIPTION OF THE DRAWINGS

For a fuller understanding of the nature and objects of the invention, reference is made to the following detailed description, taken in connection with the accompanying drawings, in which.

DETAILED DESCRIPTION OF THE PREFERRED EMBODIMENT

Figure 1:
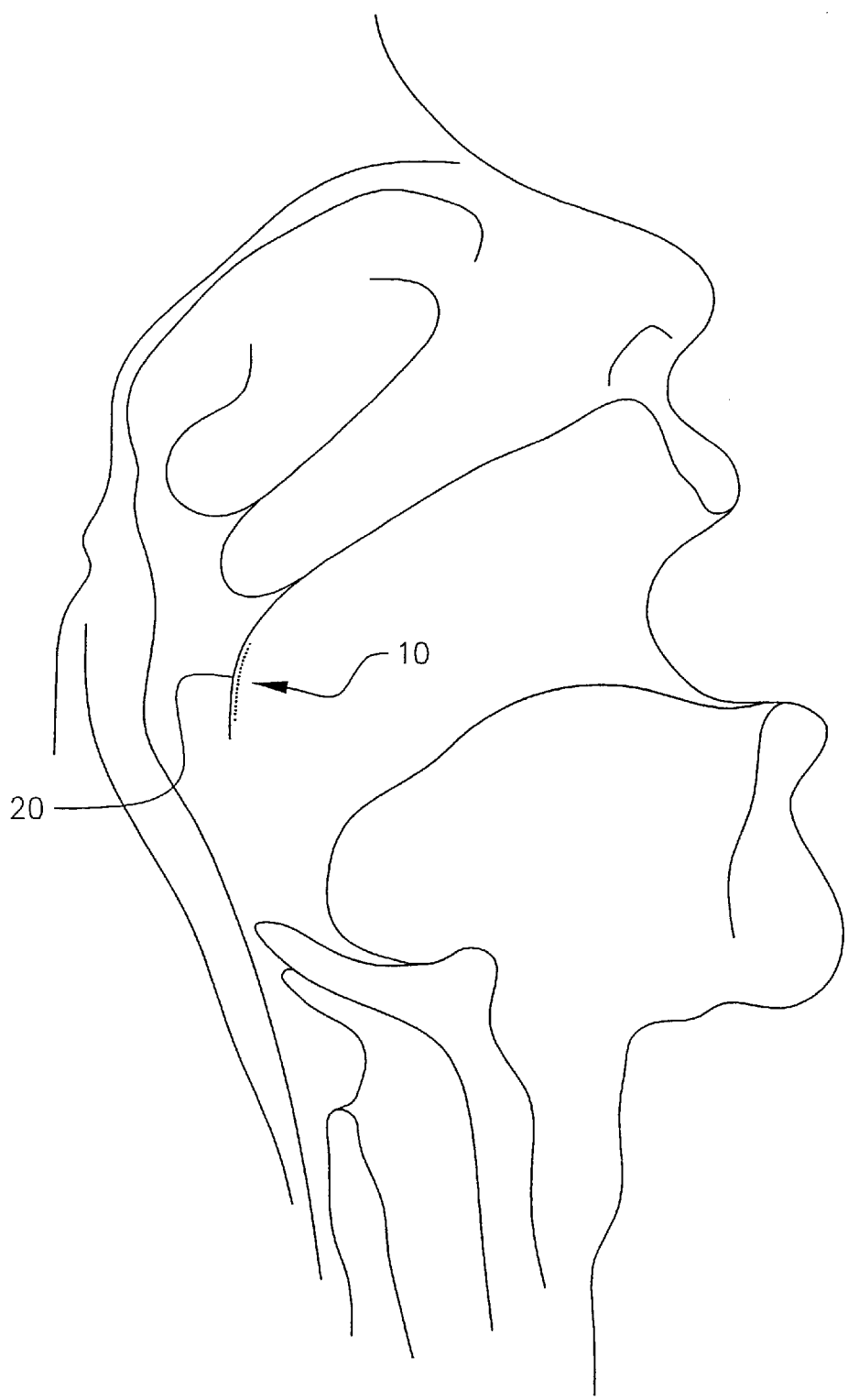
FIG. 1 is a side elevational, sectional view of a human head depicting the first embodiment of the invention.

Referring now to FIG. 1, it will there be seen that a soft pallet is denoted as a whole by the reference numeral 20. A fast-drying, non-toxic adhesive 10 is applied to soft pallet 20 by a suitable means such as an aerosol can, pump, or brush. The adhesive is preferably of the bioabsorbable type so that it is bioabsorbed within eight hours or so. Multiple layers of the adhesive may be built up in succession for those snorers requiring a higher degree of rigidity to prevent or attenuate vibration of their soft pallet.

Figure 2:
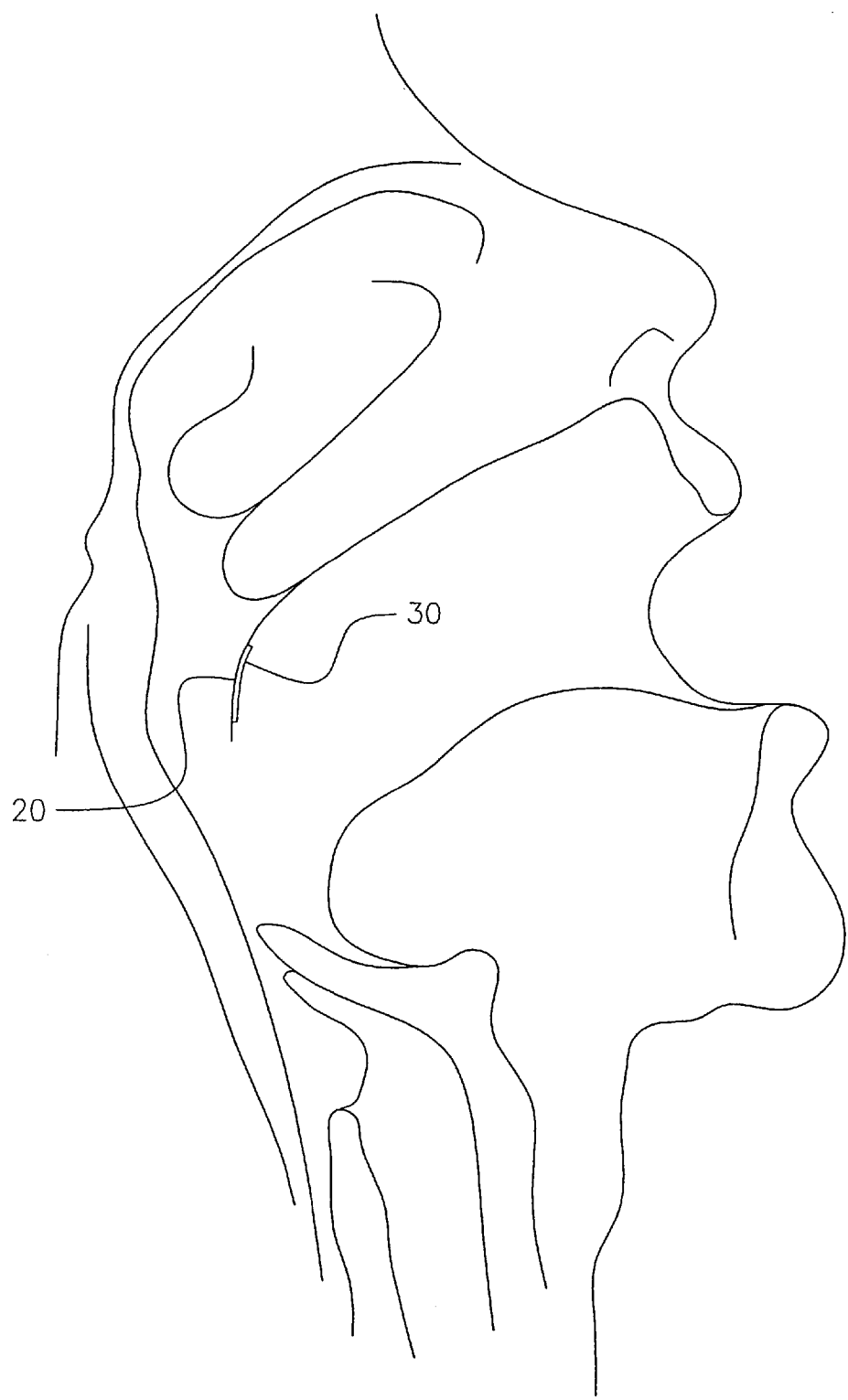
FIG. 2 is a side elevational, sectional view of a human head depicting the placement of the second embodiment.

In a second embodiment, depicted in FIG. 2, soft pallet 20 is made more rigid by application of a compound such as an astringent or muscle-contracting drug delivered by a transdermal patch denoted 30. Such a patch is preferably made of a cellulose material impregnated with a preselected astringent or muscle-contracting drug. The astringent or muscle-contracting drug makes soft pallet 20 tense or tighten up, i.e., contract or shrink, thereby inhibiting the fluttering of the soft pallet that causes snoring sounds. The compound could be provided in time-release form so that it lasts about eight hours, or it could be a compound that is released more quickly but which is effective for about eight hours.

Transdermal patch 30 could be made of a bioabsorbable material that is bioabsorbed in about eight hours so that it would be gone at the end of a sleep period. In the alternative, the transdermal patch could be made of a nonbioabsorbable material and removed at the end of a sleep period. The transdermal patch need not be applied as far back in the back of the user's throat as the adhesive of the first embodiment.

The transdermal patch of the second embodiment may be applied by an applicator of the type disclosed in co-pending patent application bearing Ser. No. 09/967,540 to the present inventor, filed Oct. 1, 2001, which patent application is hereby incorporated hereinto by reference.

In a third embodiment, the astringent or muscle-contracting drug is provided in a powder form and "snorted" by the user. In other words, the user positions the powdery substance near the nostrils and abruptly breaths in. This applies the astringent or muscle-contracting drug to the soft pallet from the upper or nasal side. FIG. 1 may be interpreted as depicting this third embodiment of the invention as well as the first embodiment thereof.

In a fourth embodiment, the astringent or muscle-contracting drug is applied to soft pallet 20 by an atomized nasal spray much such as Afrin® nasal spray. Such an application shrinks or tightens the soft pallet, stiffening it and thereby inhibiting breath-induced fluttering and the concomitant sounds of snoring. Again, FIG. 1 may be interpreted as depicting this embodiment of the invention as well as the first and third embodiments thereof.

Figure 3:
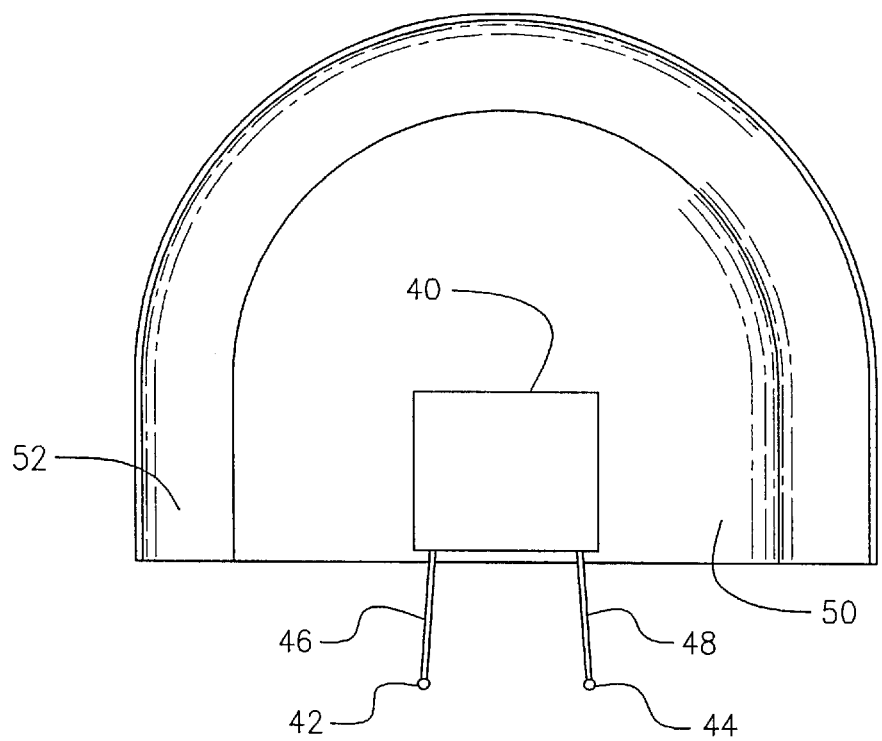
FIG. 3 is a top plan view of an electrical device that generates a low, muscle-contracting current, together with a dental device suitable for holding the electrical device in its operable position.
Figure 4:
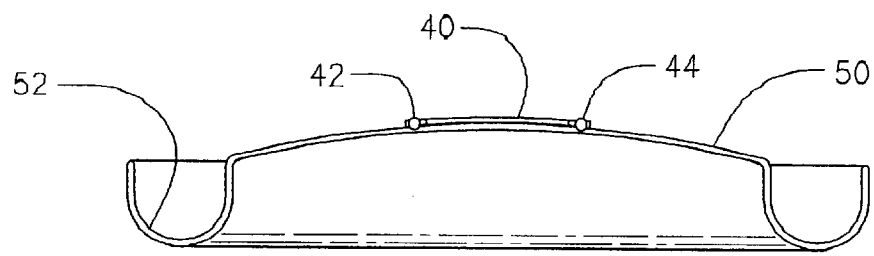
FIG. 4 is a front elevational view of the parts depicted in FIG. 3.

In a fifth embodiment, depicted in FIGS. 3 and 4, a thin, light-in-weight electrical device 40 includes a DC battery, not shown, that generates a very low current that is used to contract the muscles of the soft pallet to prevent fluttering of said soft pallet. Device 40 includes first and second electrodes 42 and 44 that are in electrical communication with device 40 by means of electrically-insulated conductors 46 and 48, respectively. One of the electrodes is hot and the other is grounded so that a very low, safe current is established between them when they are in electrical communication with the unillustrated battery means.

Electrical device 40 may be adhered to the hard pallet or it may be held thereagainst by a soft plastic, denture-like device that includes a web 50 that extends overlies the hard pallet and over electrical device 40. Web 50 is supported by a teeth-engaging, groove-shaped member 52 that fits over the upper teeth of the user. In this way, thin electrical device 40 is held in sandwiched relation between the hard pallet and web 50.

Web 50 and teeth-engaging member 52 could be permanently affixed to the hard pallet and teeth of a user, respectively, by a suitable denture adhesive.

The method of the first embodiment includes the step of applying a suitable adhesive to the soft pallet. The method of the second embodiment includes the step of applying to the soft pallet a transdermal patch treated with an astringent or muscle-contracting drug in lieu of the flexible, untreated material of the first embodiment. The method of the third embodiment includes the step of snorting a powdered form of an astringent or muscle-contracting drug. The method of the fourth embodiment includes the step of spraying an atomized mist of a suitable astringent or muscle-contracting drug upon the soft pallet and the method of the fifth embodiment includes the step of passing a very low, safe current between two closely spaced apart electrodes that are in electrically conducting relation to the soft pallet.

All of the novel methods are nonsurgical and avoid the placing of large bulky items in the mouth.

It will thus be seen that the objects set forth above, and those made apparent from the preceding description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A device that inhibits snoring, comprising:
   a transdermal patch pretreated with a muscle-contracting compound;
   said transdermal patch disposed in overlying relation to a soft pallet;
   whereby said muscle-contracting compound causes contraction of said soft pallet so that said soft pallet does not flutter when a user is breathing.

2. The device of claim 1, wherein said compound is an astringent.

3. The device of claim 1, wherein said compound is a muscle-contracting drug.

4. The device of claim 1, wherein said compound is released over a preselected period of time.

5. The device of claim 1, wherein said transdermal patch is bioabsorbable.

* * * * *